(12) United States Patent
Chauvin et al.

(10) Patent No.: US 6,525,228 B2
(45) Date of Patent: Feb. 25, 2003

(54) PROCESS OF TELOMERIZING CONJUGATED DIENES

(75) Inventors: Yves Chauvin, Tours (FR); Lionel Magna, Hyeres (FR); Gerald Peter Niccolai, Villeurbanne (FR); Jean-Marie Basset, Caluire (FR)

(73) Assignee: Celanese Chemicals Europe GmbH, Frankfurt (DE)

( * ) Notice: Subject to any disclaimer, the term of this patent is extended or adjusted under 35 U.S.C. 154(b) by 0 days.

(21) Appl. No.: 10/036,265

(22) Filed: Oct. 22, 2001

(65) Prior Publication Data

US 2002/0091281 A1 Jul. 11, 2002

(30) Foreign Application Priority Data

Oct. 27, 2000 (EP) .............................. 00123528

(51) Int. Cl.$^7$ ............................... C07C 41/01
(52) U.S. Cl. ..................... 568/687; 568/689; 568/690
(58) Field of Search ................................ 568/687, 689, 568/690

(56) References Cited

U.S. PATENT DOCUMENTS 4,142,060 A   2/1979   Kuntz ....................... 568/840

FOREIGN PATENT DOCUMENTS

EP   0613875   9/1994
FR   2719580   5/1994

OTHER PUBLICATIONS

Dullius et al., "Selective Catalytic Hydrodimerization of 1,3–Butadiene by Palladium Compounds Dissolved in Ionic Liquids," Organometallics 1998, vol. 17, No. 5, pp. 815–819, XP–002190802.

European Search Report for EP01123111 dated Mar. 7, 2002.

*Primary Examiner*—Rosalynd Keys
(74) *Attorney, Agent, or Firm*—Rankin, Hill, Porter & Clark LLP

(57) ABSTRACT

The present invention is related to a process for telomerizing a conjugated diene which comprises reacting said conjugated diene with a compound containing active hydrogen in the presence of a catalyst system comprising at least one transition metal compound, at least one phosphorus-containing compound, and at least one salt which forms a liquid under the conditions of the telomerization process.

10 Claims, 1 Drawing Sheet

PROCESS OF TELOMERIZING CONJUGATED DIENES

DESCRIPTION

The present invention is related to a new process for telomerizing conjugated dienes and a new composition useable in the telomerization of conjugated dienes.

The catalytic dimerization of dienes under the concomitant addition of a nucleophilic reagent was reported simultaneously in 1967 by Smutny at Shell and Takahashi at Osaka University. The reaction is defined under the general term of telomerization as the dimerisation of conjugated diolefins (taxogens) together with the addition of a third molecule (telogen) over one double bond equivalent. Telogens can be for example alcohol, amine (I and II), methylene group, silane, carboxylic acid, water, etc. (see scheme 1) leading to heavier organics (ethers, amines, silanes, esters, alcohols, etc.).

The telomerization of butadiene with methanol (MeOH) has been extensively investigated. While some activity was observed for a variety of metals, cobalt, rhodium, nickel, and platinum, palladium based systems are superior both in terms of activity and selectivity. Conventional systems commonly associate a mixture of palladium(II) and phosphine ligands and lead mainly to the formation of trans and cis-1-methoxy-2,7-octadiene (t-I and c-I) and 3-methoxy-1,7-octadiene (II) and the octatriene III as a by-product (see for example U.S. Pat. No. 4,142,060).

Scheme 2

Telomerization of butadiene and methanol

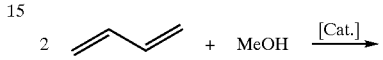

Scheme 1

Telomerization of butadiene with different nucleophiles

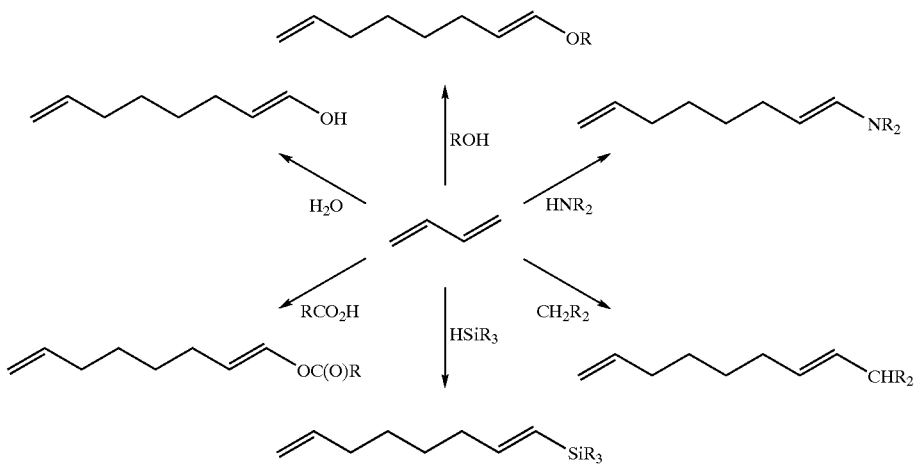

For example U.S. Pat. No. 4,142,060 is related to a process of telomerizing dienes with a telomerizing compound (e.g. methanol, water, etc.), comprising the reaction of a diene with a telomerizing compound with at least one mobile hydrogen atom in the presence of a water-soluble catalytic system comprising at least one certain water-soluble phosphine and a transition metal, preferably palladium or a palladium containing compound.

WO 98/08794 discloses a process for telomerizing dienes with a telogen containing a reactive hydrogen atom in the presence of a palladium compound and a specific water-soluble phosphine.

Using water as a telogen the reaction with butadiene is usually designated as hydrodimerization. The telomerization of butadiene with water is described for example in U.S. Pat. Nos. 5,043,487, 5,345,007, 4,356,333, EP-A-0,436,226, WO 95/30636 and U.S. Pat. No. 4,417,079.

-continued

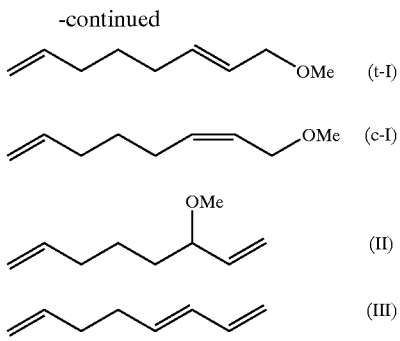

Telomerization of 1,3-butadiene with an alcohol has recently gained increasing interest for the synthesis of linear ethers. These products, after hydrogenation of the remaining olefinic double bonds, can be particularly useful as fuel additives or plasticizers.

Scheme 3

Synthesis of linear saturated ethers

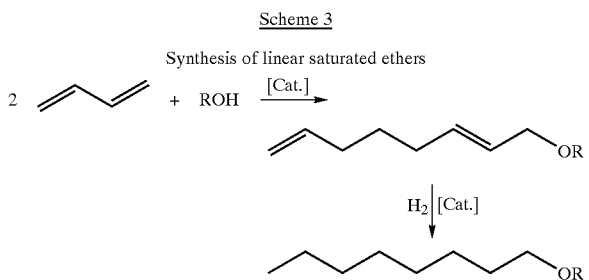

Works described in the last twenty years concentrate on the study of the reaction under homogeneous conditions. The separation of the homogeneous catalysts, typically palladium based, from the products is a significant factor in the economics of the application of this powerful reaction. It is now generally accepted that the use of two-phase catalytic systems is an approach that could overcome of the separation problems by allowing the phase separation of the products from the catalyst phase.

Recently, non-aqueous ionic liquids have been attracting attention for the application of many homogeneous reactions to biphasic systems (see for example the reviews "Ionic Liquids" of J. D. Holbrey, K. R. Seddon in Clean Products and Processes 1 (1999) 223–236 and Welton, T. *Chem. Rev.* 1999, 99, 2071–2083).

EP-A-0,776,880 (corresponding to U.S. Pat. No. 5,874, 638) discloses for example a process for the hydroformylation of olefinic compounds in the presence of an ionic liquid.

J. Dupont et al. (Organometallics 1998, 17, 815–819) disclose a catalytic process of hydrodimerization of 1,3-butadiene by palladium compounds dissolved in ionic liquids. As palladium catalyst compounds [($\eta^3$-$C_4H_7$)Pd-$\mu$-Cl]$_2$, [($\eta^3$-$C_4H_7$)Pd(1,5-cyclooctadiene)][$BF_4$] and palladium acetate have been used which are told to be completely soluble and stable in the ionic liquids 1-n-butyl-methylimidazolium tetrafluoroborate ($BMI^+$.$BF_4^-$) and 1-n-butyl-methylimidazolium hexafluorophosphate ($BMI^+$.$PF_6^-$) at room temperature. At the end of the performed hydrodimerization reactions however metallic palladium was detected thus limiting the reutilization of the catalytic system. This has been attributed to the instability of these catalysts to water. The formation of metallic palladium could be suppressed by the use of a new catalyst precursor $(BMI)_2PdCl_4$ which has been obtained by reacting $PdCl_2$ with a 2 molar excess of 1-n-butyl-3-methylimidazolium chloride in acetonitrile at reflux temperature. However even for this stable catalyst conversions reported were low.

In an attempt to use conventional palladium phosphine catalysts in the presence of ionic liquids such as the above mentioned 1-n-butyl-methylimidazolium tetrafluoroborate ($BMI^+$.$BF_4^-$) or 1-ethyl-3-methylimidazolium bis (trifluoromethanesulfonyl)imide ($EMI^+$.$TF_2N^-$) for the telomerization of butadiene for example with methanol, the present inventors found surprisingly that the conventional palladium phosphine catalyst system in the presence of ionic 1,3-dialkylimidazolium liquids in contrast to the above mentioned catalyst compounds like [($\eta^3$-$C_4H_7$)Pd-$\mu$-Cl]$_2$, [($\eta^3$-$C_4H_7$)Pd(1,5-cyclooctadiene)][$BF_4$] or palladium acetate shows almost no reactivity, and thus was not available for a telomerization process in the presence of the ionic liquid.

The object underlying the present invention was to find a new catalytic process for telomerizing a conjugated diene wherein a highly active and selective catalyst system can be used which allows the formation of the diene telomers with high yields and selectivity and which also allows a simple separation and recycling of the catalyst system.

In accordance with the present invention there is provided a new process for telomerizing a conjugated diene which comprises reacting said conjugated diene with a compound containing active hydrogen in the presence of a catalyst system comprising at least one transition metal compound, at least one phosphorus-containing compound, and at least one salt which forms a liquid under the conditions of the telomerization process.

Figure 1:
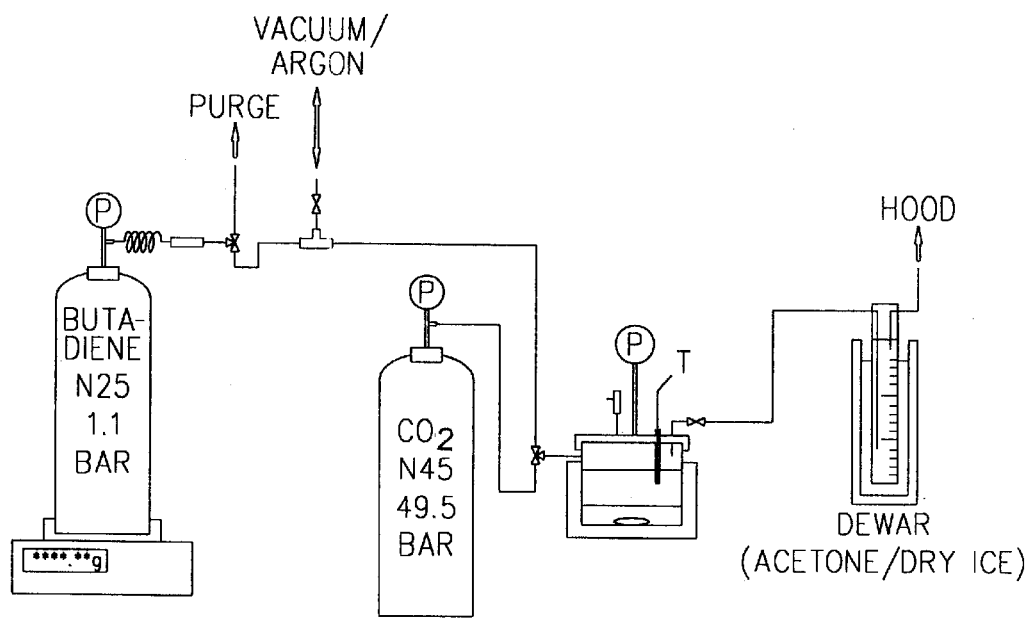
FIG. 1 shows the apparatus for telomerizing butadiene which has been used in the examples.
Figure 2:
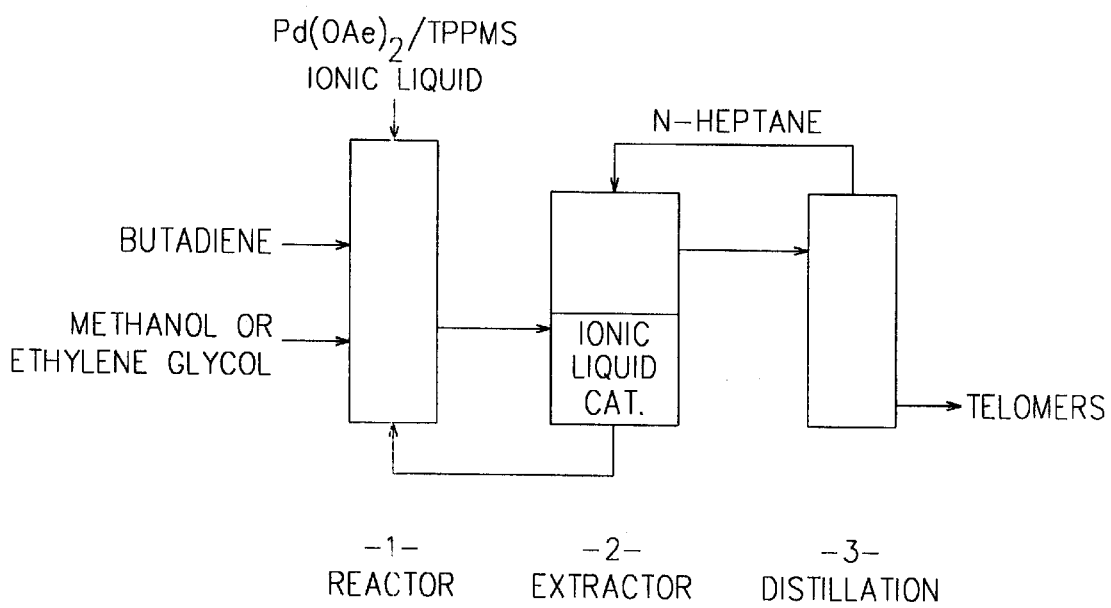
FIG. 2 shows an embodiment of a two-phase process of telomerization of butadiene ($C_4H_6$) with MeOH or ethylene glycol in ionic liquids.

The conjugated diene preferably has 4 to 6 carbon atoms. Particularly preferred the conjugated diene is selected from butadiene, isoprene or 1,3-pentadiene. The most preferred conjugated diene is butadiene.

The compound containing active hydrogen is usually referred to in the art as telogen. It is preferably a compound of the general formula (I)

H—A wherein A is selected from the group consisting of hydroxy, alkoxy, cycloalkoxy, alkoxy substituted with one or two hydroxy groups, hydroxypolyalkyleneoxy, alkenyloxy, aryloxy, alkanoyloxy, mono- or dialkylamino, tri(alkyl- and/or aryl)silyl, and an alkyl group substituted in the a-position with at least one electron attracting group, preferably selected from alkoxycarbonyl, alkanoyl and/or cyano, wherein the above mentioned alkyl moieties independently from each other are branched or linear and each may have up to 8 carbon atoms, and wherein the above mentioned aryl moieties independently from each other may have up to 10 carbon atoms.

Thus the compound containing active hydrogen includes for example: in case of A being hydroxy, water as the telogen; in case of A being alkoxy, alkanols as the telogen, like methanol, ethanol, n-propanol, isopropanol, n-butanol, isobutanol, sec. butanol etc.; in case of A being cycloalkoxy, cycloalkanols as the telogen, like cyclohexanol etc.; in case of A being alkoxy substituted with one hydroxy group, alkane diols as the telogen, like glycol, 1,2- or 1,3-propandiol etc.; in case of A being alkoxy substituted with two hydroxy groups, alkane triols as the telogen, like e.g. glycerol etc.; in case of A being hydroxypolyalkylene oxy, compounds of the formula HO—[alkyleneoxy]$_x$—H wherein alkylene independently (different alkylene moeities may be in one molecule) has up to 6 carbon atoms and includes for example ethylene, propylene and butylene, and x is in average between 2 and 10 like, for example, diethylene glycol etc.; in case of A being alkenyloxy, alkenols as the telogen, like allyl alcohol etc., in case of A being aryloxy, aromatic alcohols as the telogen, like phenol, naphthols etc., in case of A being alkanoyloxy, carboxylic acids as the telogen, like acetic acid etc., in case of A being mono- or dialkylamino, amines as the telogen, like primary or secondary amines like methyl amine, ethyl amine, dimethyl amine, diethyl amine etc., in case of A being tri(alkyl- and/or aryl)silyl, tri(alkyl- and/or aryl)silanes as the telogen, like trimethyl silane, triethyl silane, triphenyl silane, phenyldimethyl silane etc., and in case of A being an alkyl group substituted in the α-position with at least one electron attracting group, preferably selected from alkoxycarbonyl, alkanoyl and/or cyano, CH-acidic compounds with activated methylene groups (so-called "Michael-Donors") as the telogen, like malonic acid dialkyl esters, acetic acid alkyl esters etc.

Particularly preferred telogens are water, methanol and glycol, and most preferred is methanol.

The transition metal compound which forms part of the catalyst system of the invention can be any transition metal compound suitable for catalysis of the telomerization reaction in the presence of the phosphorous compound and the salt. Preferably it is a compound of an element of the group VIIIB (or 8, 9 and 10) of the periodic system of elements, that is a compound of iron, cobalt, nickel, ruthenium, rhodium, palladium, osmium, iridium or platinum. More preferred compounds are selected from compounds of cobalt, rhodium, nickel, platinum and palladium. Concerning possible transition metal compounds for carrying out the telomerization process it is referred to A. Behr in "Aspect of Homogeneous Catalysis, A Series of Advances; Edited by R. Ugo; D. Reidel Publishing Company; Vol. 5; p3–73; 1984"/ Tsuji, J. *Adv. Organomet. Chem.* 1979, 17, 141/W. Keim: in <<Transition Metals in Homogeneous Catalysis>>, Ed. G. N. Schrauzer, p 59, Marcel Dekker, New York, 1971/R. Baker, *Chem. Rev.*, 73, 487, 1973/and P. N. Rylander in <<Organic Chemistry>>, vol 28, p 175, Academic Press, New York, 1973.

Most preferred are palladium compounds, for example, known palladium compounds used in telomerization processes for example those described in U.S. Pat. Nos. 5,043,487, 4,356,333, 4,142,060, EP-A-0,436,226, WO 98/08794, WO 96/30636 and U.S. Pat. No. 4,417,079 the relevant content of which is herein incorporated by reference.

Examples of these palladium compounds include soluble palladium(0) and palladium(II) compounds, for example, palladium acetylacetonate, π-allylpalladium acetate, π-allylpalladium chloride, palladium acetate, palladium carbonate, palladium nitrate, palladium chloride, sodium chloropalladate, bis(benzonitrile)palladium chloride, bis(triphenylphosphine)palladium chloride, bis(triphenylphosphine)palladium acetate, bis(1,5-cyclooctadiene)palladium and bis(π-allyl)palladium.

A particular preferred palladium compound is palladium acetate (Pd(OAc)$_2$).

The active species of the transition metal compound is a low-valence transition metal complex which may be formed by reduction in the presence of butadiene or by suitable reducing agents added.

The ratio of the transition metal compound to the conjugated diene is not critical, but is preferably from $10^{-5}$ to $10^{-1}$, in particular from $10^{-4}$ to $10^{-2}$, mol of the transition metal per mole of the conjugated diene.

The phosphorus-containing compound which forms part of the catalyst system is not particularly restricted but can be any phosphorus-containing compound, capable of coordinating to the transition metal compound, for example hydrophobic or hydrophilic, water-soluble, mono- or bidentate phosphorus-containing compounds known for telomerization processes (e.g. those known from U.S. Pat. Nos. 5,043,487, 5,345,007, 4,356,333, EP-A0436226, WO98/08794, WO95/30636, U.S. Pat. Nos. 4,417,079 and 4,142,060 the relevant content of which is herein incorporated by reference).

Suitable examples include phosphines or phosphites, preferably mono- or bidentate alkylphosphines, arylphosphines, arylalkylphosphines, alkylphosphites, arylphosphites, and arylalkylphosphites, wherein the hydrocarbon moieties independently each may have up to 36 carbon atoms, preferably 24 carbon atoms, more preferably 10 carbon atoms and may be substituted by one to three suitable substituents preferably selected from a sulfonic acid group or a salt thereof, a carboxylic acid group or a salt thereof, an (C1–C10)alkyl group optionally substituted with a sulfonic acid group or a salt thereof or a carboxylic acid group or a salt thereof, and an (C6–C10)aryl group optionally substituted with a sulfonic acid group or a salt thereof or a carboxylic acid group or a salt thereof. Salts of the sulfonic acid or carboxylic acid group include for example alkali metal salts like sodium or potassium salts and ammonium salts. The aforementioned optionally substituted alkyl groups including the (C1–C10)alkyl group include linear or branched alkyl groups having 1 to 10 carbon atoms (C1–C10), such as methyl, ethyl, n-propyl, isopropyl, n-butyl, iso-butyl, sec. butyl, tert.-butyl, n-pentyl, iso-pentyl, neopentyl, n-hexyl, n-heptyl, n-octyl, n-nonyl and n-decyl. Preferred are alkyl groups with up to 6 carbon atoms. The aforementioned optionally substituted aryl groups including the (C6–C10)aryl group include for example phenyl, tolyl, naphtyl, etc.

Examples of these phosphines or phosphates include tributylphosphine, dimethyl-n-octylphosphine, tricyclohexylphosphine, triphenylphosphine (TPP), tritolylphosphine, tris(p-methoxyphenyl)phosphine, diphenylethylphosphine, dimethylphenylphosphine, 1,2-bis-diphenylphosphinoethane, triethyl phosphite, tricyclohexyl phosphite and triphenylphosphite, hydrophilic arylphosphines, like sulfonated or carboxylated arylphosphines, preferably water-soluble salts of mono-, di- or trisulfonated triphenylphosphine compounds like trisodium tris(m-sulfonatophenyl)phosphine) (TPPTS), bis(p-sulfonatophenyl)phenylphosphine dihydrate dipotassium salt (TPPDS) and diphenylphosphinobenzene-3-sulfonic acid sodium salt (TPPMS).

Suitable sulfonated phosphine compounds are for example those of the following formula disclosed in U.S. Pat. No. 4,356,333:

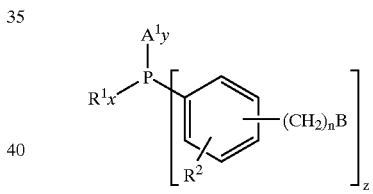

wherein R$^1$ is an aliphatic, alicyclic or substituted or unsubstituted aromatic hydrocarbon group having 1 to 8 carbon atoms; R$^2$ is hydrogen, methyl, nitro, cyano, methoxy or halogen; n is 0 or 1, x is 0, 1 or 2, and y and z are each 0, 1, 2 or 3, with the proviso that y and z are not concurrently equal to 0 and that x+y+z=3;

A$^1$ is

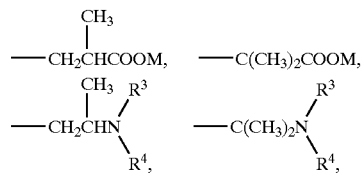

a carbonate or bicarbonate of

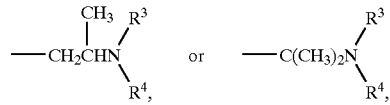

and B is

or a carbonate or bicarbonate of

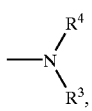

wherein $R^3$ and $R^4$ are each methyl ethyl or n-propyl and M is an alkali metal, further those disclosed in U.S. Pat. No. 4,142,060 of the following formula:

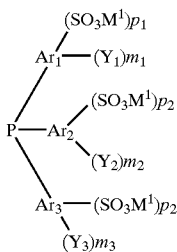

wherein $Ar_1$, $Ar_2$ and $Ar_3$ each represent an aryl group having from 6 to 10 carbon atoms, which may be alike or different from each other; $Y_1$, $Y_2$ and $Y_3$, which may be alike or different from each other each represent an alkyl group containing 1 to 4 carbon atoms, an alkoxy group containing 1 to 4 carbon atoms, a halogen, cyano-, nitro-or hydroxy radical or an amino group

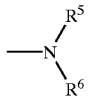

wherein $R^5$ and $R^6$, which may be alike or different from each other each represent an alkyl group containing 1 to 4 carbon atoms; $M^1$ represents a cation selected from the group consisting of a proton, a cation derived from an alkali metal or an alkaline earth metal, ammonium, a group $N(R^7R^8R^9R^{10})^+$ wherein $R^7$, $R^8$, $R^9$ and $R^{10}$ each represent hydrogen or an alkyl group containing 1 to 4 carbon atoms and may be alike or different from each other, and a cation of any other metal, which is able to form water-soluble salts with benzosulfonic acids; $m_1$, $m_2$ and $m_3$ each represent a whole number from 0 to 5 which may be the same or different from each other, and $p_1$, $p_2$ and $p_3$ each represent a whole number from 0 to 3, which may be the same or different from each other, whereby at least one of these numbers $p_1$, $p_2$ and $p_3$ equals at least one.

Suitable sulfonated arylalkylphosphines are disclosed for example in WO95/30636.

Suitable bidentate, water-soluble phosphine compounds include, in particular, the compounds disclosed in WO98/08794 of the following formula:

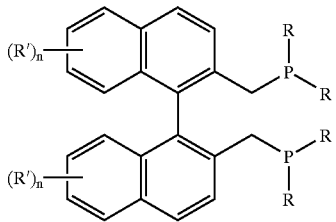

in which the R groups are identical or different and designate phenyl, C1–C12 alkyl and C3–C10 cycloalkyl, which can optionally be substituted with one or a plurality of R' groups, the R' groups, which are identical or different, designate $-SO_3^-M^2$, $-N(CH_3)_3^+$, $-COO^-M$, n is an integer from 1 to 6, in each case relative to a naphthyl structure, and $M^2$ designates $H^+$, $Na^{+, K+}$, $Cs^+$ and $R''_4N^+$, the R'' groups being identical or different and designating H, C1–C12 alkyl, C1–C10 cycloalkyl.

Usually the phosphorus-containing compound and the ionic liquid compound form different components. However, in case the phosphorus-containing compound carries a negative charge, for example, in the form of a sulfonate or carboxylate group, it is possible that it forms the anion of the ionic liquid compound, and this case shall be included within the scope of the present invention. Such phosphorus-containing ionic liquid compounds can also be used together with further phosphorus-containing compounds and ionic liquid compounds respectively, mentioned before. Suitable phosphorus-containing ionic liquid compounds are known in the art, and are for example disclosed in EP-A-0924218 (U.S. Pat. No. 6,103,908). EP-A-0924218 discloses nonaqueous ionic ligand liquids of the formula $(Q^\oplus)_aA^{a-}$, wherein $Q^\oplus$ is a singly charged quaternary ammonium and/or phosphonium cation or the equivalent of a multiply charged ammonium and/or phosphonium cation and $A^{a-}$ is a triarylphosphine anion of the formula:

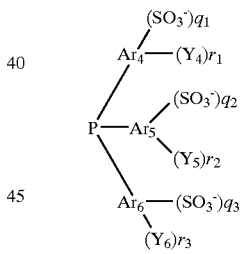

where $Ar_4$, $Ar_5$ and $Ar_6$ are individually aryl of 6 to 14 carbon atoms, the substituents $Y_4$, $Y_5$ and $Y_6$ are individually selected from the group consisting of alkyl and alkoxy of 1 to 4 carbon atoms, chlorine, bromine, hydroxyl, cyano, nitro and amino groups of the formula $-NR^{11}R^{12}$, where $R^{11}$ and $R^{12}$ are individually hydrogen or alkyl of 1 to 4 carbon atoms, $r_1$, $r_2$, and $r_3$ are individually integers from 0 to 5, $q_1$, $q_2$ and $q_3$ are individually integers from 0 to 3, where at least one of $q_1$, $q_2$ and $q_3$ is equal to or greater than 1, and a is $q_1+q_2+q_3$, and amines and/or phosphines derived from $Q^\oplus$ are present in an excess of up to 5 equivalents over the stoichiometrically required amount for the formation of $(Q\oplus)_aA^{a-}$ or alkali metal or alkaline earth metal salts of the triarylphosphines $A^{a-}$ are present in an excess of up to 5 equivalents over the stoichiometrically required amount for the formation of $(Q^\oplus)_aA^{a-}$.

Similarly not prior published German patent application no. 19919494.7 (corresponding to international patent application no. PCT/EP00/03499) discloses suitable nonaqueous ionic ligand liquids of the formula $(Q_1^{\oplus})_b A^{'c-}$, wherein $Q_1^{\oplus}$ is a singly charged ammonium cation, optionally substituted with organic group(s), or the equivalent of a multiply charged ammonium cation and $A^{'c-}$ is an anion of a sulfonated or carboxylated triester of phosphorous acid and c is an integer of at least one. These ammonium salts of sulfonated or carboxylated phosphorous acids may be formally derived from phosphorous acid by esterification with the ammonium salts of hydroxysulfonic acids or hydroxycarboxylic acids of the following general formula

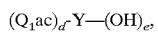

$(Q_1 ac)_d\text{-}Y\text{-}(OH)_e,$ wherein ac is the acidic residue, namely the sulfonic acid residue $—SO_3^-$, and the carboxylic acid residue, respectively and $Q_1$ is as already mentioned a singly charged ammonium cation, optionally substituted with organic group (s), or the equivalent of a multiply charged ammonium cation, Y represents an organic residue and is preferably a branched or non-branched saturated aliphatic hydrocarbon group having a total of up to 20 carbon atoms, optionally substituted by hydroxy or C1–C10 alkoxy, d an e are integers of at least 1, e is preferable 1 or 2.

In general, the phosphines are preferred to the phosphites since the latter depending on the telogen used may undergo hydrolysis and rearrangement reactions. Particularly preferred are sulfonated aryl phosphine compounds like the above mentioned TPPTS, TPPDS and TPPMS.

The amount of these phosphorus-containing compounds is in general from 1 to 100, preferably from 1 to 10, mol per mole of the transition metal.

Depending on the telogen, to be telomerized, the phosphorus-containing compound used as the catalyst component and the relative amounts of the reactants in some instances mono phasic reaction systems may be formed. These mono phasic reaction systems can be usually transferred into biphasic systems by the addition of at least one non-polar solvent (usually a solvent which is immiscible with water). Thereby a phase consisting of the solvent and the product (usually the upper phase) and a phase consisting of the salt (or ionic liquid) and the major part of catalyst (usually the lower phase) is formed. In some cases, depending on the telogen used and the catalyst system part of the catalyst may be contained also in the product phase. The non-polar solvent may include for example aliphatic hydrocarbons, for example alkanes like pentane, hexane, heptane and octane etc., cycloalkanes like cyclopentane, cyclohexane etc., aromatic hydrocarbons like benzene, toluene, xylene etc. and aliphatic or aromatic ethers, like diethyl ether, tetrahydrofuran, anisol, methyl tert.-butyl ether (MTBE), ethylene glycol, dimethoxyethane, etc. A particular preferred non-polar solvent is n-heptane.

The non-polar solvent may be added at any stage of the reaction depending on its possible influence on the telomerization reaction. Preferably it is however added after the reaction and preferably in those cases where monophasic reaction systems are formed.

In a typical embodiment of carrying out the process according to the invention a conjugated diene is reacted with a compound containing active hydrogen in the presence of a catalyst system comprising at least one transition metal compound, at least one phosphorus-containing compound, and at least one salt which forms a liquid under the conditions of the telomerization process, optionally at least one non-polar solvent during or after the reaction is added, the product phase and the salt phase comprising the catalyst system are separated and the salt phase comprising the catalyst system is recycled in the telomerization reaction.

Depending on the telogen the desired products are for example trans- and cis-1-methoxy-2,7-octadiene and 3-methoxy-1,7-octadiene for methanol, cis- and trans 2,7-octadiene-1-ol and 1,7-octadiene-3-ol for water, and 1-hydroxy-2-(2,7-octadienyl-1-oxy)ethane, 1-hydroxy-2-(1, 7-octadienyl-3-oxy)ethane, and bis(octadienyl-1-oxy)-1,2-ethane for glycol.

The obtained unsaturated products can be hydrogenated catalytically into the corresponding saturated compounds in a known manner.

The telomerization reaction is usually performed under a pressure of from normal pressure to 200 bar, preferably from normal pressure to 30 bar.

The temperature of the telomerization reaction is usually in the range of 20 to 200° C., preferable of 30 to 180° C., more preferable of 40 to 140° and still more preferable of 50 to 120° C.

The amount of the transition metal is usually in the range of 1 to 200 mM per liter of the ionic liquid and more preferably 10 to 50 mM per liter of the ionic liquid.

The amount of the phosphorus-containing compound is usually in the range of 1 to 100, preferably from 1 to 10 mole per mole of the transition metal.

The amount of the salt (ionic liquid) in the reaction system is usually in the range of 5 to 100 parts per 100 parts of the diolefin, preferably 10 to 50 parts per 100 parts of the diolefin.

The molar ratio of telogen/conjugated diene is usually in the range of 0.5 to 10, preferably 0.5 to 5.

As generally known the hydrodimerization with water as the telogen is preferably carried out in the presence of a base and under $CO_2$-pressure. Suitable bases include for example the hydroxides of alkali metals and alkaline earth metals and amines. Suitable amines include for example tertiary amines having a basicity constant (pKa) of at least 7, for example tri(C1–C6)alkylamines such as trimethylamine, triethylamine, tri-n-propylamine, tri-n-butylamine, etc.; and N,N-dimethyl-2-methoxyethylamine, N,N-dimethyl-3-ethoxypropylamine, N-methylpyrrolidine, N-methylpiperidine, N-methylmorpholine, N,N'-dimethylpiperazine, N,N,N',N'-tetramethyl-1,3-butanediamine and the like. Among these, triethylamine is most preferred.

Further carbonate and/or bicarbonate ions may be present along with the tertiary amine to accelerate the rate of n-octadienol formation. Carbonate and bicarbonate ions are conveniently derived from carbon dioxide, sodium bicarbonate or formic acid which releases these ions in the reaction system. Among these, carbon dioxide is most preferred.

The amount of carbon dioxide which promotes the butadiene telomerization is not critical and may range from about $10^{-3}$ to 1, preferably from $10^{-2}$ to 0.5, mol per mole of the conjugated diene.

In contrast to the conventional processes the telomerization process according to the invention is carried out in the presence of at least one salt which forms a liquid under the conditions of the telomerization process. These salts are commonly designated as "ionic liquids". Such an ionic liquid serves mainly as a solvent for the catalyst components. In some cases it can be also catalytically active, in particular, if it belongs to the group of ionic liquids having a phosphorus-containing anion. Preferably the salt to be used in the process of the invention does not substantially deactivate the catalyst system.

Usually the salt or ionic liquid has a melting point of below 200° C., preferable below 160° C., more preferable below 140° C., still more preferable below 120° C., and most preferable below 100° C., in particular, below 90° C. The melting points are measured at normal pressure with a digital apparatus such as of Electrothermal.

Ionic liquids to be used in the process of the present invention include preferably 1,2,3-substituted imidazolium salts, 1,2,3,4-substituted imidazolium salts, 1,2,3,4,5-substituted imidazolium salts and 1-substituted pyridinium salts.

Suitable 1-substituted pyridinium salts include preferably 1-alkyl-substituted pyridinium salts having up to 10 preferable up to 6 carbon atoms in the alkyl moiety. The most preferred 1-substituted pyridinium salts are n-butyl pyridinium salts like n-butyl pyridinium hexafluorophosphate (melting point 78–79° C.).

Among the imidazolium salts the compounds of the following formula are preferred:

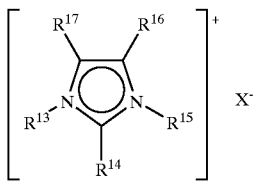

wherein $R^{13}$ and $R^{15}$ are the same or different and are each selected from the group consisting of an alkyl group having up to 10, preferable up to 6 carbon atoms, an aryl group of 6 to 10 carbon atoms, and a tri(C1–C6)allylsilyl group, $R^{14}$ is selected from the group consisting of an alkyl group having up to 10, preferable up to 6 carbon atoms, and an aryl group of 6 to 10 carbon atoms, $R^{16}$ and $R^{17}$ are the same or different and are each selected from the group consisting of hydrogen, an alkyl group having up to 10, preferable up to 6 carbon atoms, an aryl group of 6 to 10 carbon atoms, a tri(C1–C6) alkylsilyl group and a halogen atom, and $X^-$ represents an anion.

The aforementioned alkyl group having up to 10, preferable up to 6 carbon atoms in the definitions of $R^{13}$ to $R^{17}$ includes linear or branched alkyl groups, such as methyl, ethyl, n-propyl, isopropyl, n-butyl, iso-butyl, sec. butyl, tert.-butyl, n-pentyl, iso-pentyl, neopentyl, n-hexyl, n-heptyl, n-octyl, n-nonyl and n-decyl. Preferred are alkyl groups with up to 6 carbon atoms.

The aforementioned (C6–C10)aryl group includes for example phenyl, tolyl, naphtyl, etc.

With respect to the above mentioned (C1–C6)alkyl moiety of the tri(C1–C6)alkylsilyl group it is referred to the C1–C6 alkyl groups for $R^{13}$ to $R^{17}$.

Imidazolium salts are known in the art. For example EP-A-0404179 and EP-A-0398358 disclose 1,2,3-trialkylimidazolium halides as an electrolyte. WO 00/32572 which is related to combinatorial material science discloses an array comprised of a plurality of members with each member comprising an ionic liquid characterized by the general formula $A^+B^-$ where $A^+$ represents any stable inorganic or organic cation and $B^-$ represents any stable organic or inorganic anion wherein $A^+$ includes imidazolium cations.

Regarding the process of manufacture of the 1,2,3-trialkylimidazolium salts the following two synthesis routes have been followed. In the first, the 1,2-dialkylimidazole (generally commercial products) are alkylated with an organic halide and the desired salt is then obtained by an anion exchange reactions (metathesis). In the second, the liquid could be obtained directly by the quaternization of an 1,2-dialkylimidazole with the alkylating agent itself providing a suitable anion.

Scheme

Synthesis routes of imidazolium ionic liquids

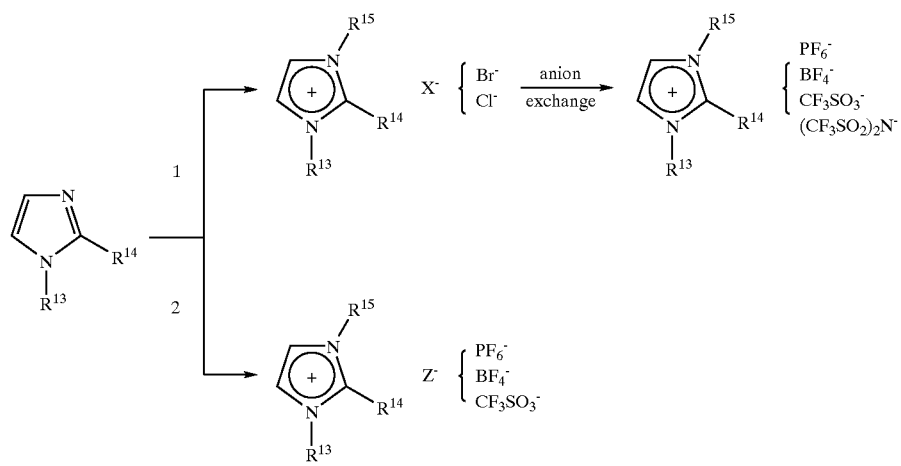

In the prior art the indirect route (1) is by far the most widely studied.(P. Bonhote, A.-P. Dias, N. Papageorgiou, K. Kalyanasundaram, Gratzel, M. Inorg. Chem. 1996, 35, 1168–1178) (J. S. Wilkes, M. J. Zaworrotko, J. Chem. Soc., Chem. Commun. 1992, 965–967) (J. Fuller, R. T. Carlin, R. A. Osteryoung, J. Electrochem. Soc. 1997, 144, 3881–3886) Generally, bromide or chloride imidazolium are used as intermediate in the synthesis of the final ionic liquid.

The anion exchange involved in the second step can be performed in different solvents. Water (J. D. Holbrey, K. R. Seddon, J. Chem. Soc., dalton Trans. 1999, 2133–2139) and acetone (P. A. Suarez, J. E. L. Dullius, S. Einloft, R. F. de Souza, J. Dupont, Polyhedron, 1996, 15, 1217–1219) (P. A. Suarez, S. Einloft, J. E. L. Dullius, R. F. de Souza, J. Dupont, J. Chim. Phys., 1998, 95, 1626–1639) can be used.

On the other hand, the direct synthesis route (Scheme, 2) allows one to obtain an ionic liquid without any addition of halide by the reaction of an N-alkylimidazole with an appropriate alkylating agent. The alkylating agent must be able to realize both the quaternarization of the imidazole ring and the introduction of a non-coordinating anion.

In the prior art alkylating agents derived from alkyltriflates (methyl and ethyltriflate) were until recently exclusively described (P. Bonhote, A.-P. Dias, N. Papageorgiou, K. Kalyanasundaram, Gratzel, M. Inorg. Chem. 1996, 35, 1168–1178). Reaction is carried out in refluxing of 1,1,1-trichloroethane, a solvent chosen for its stability toward strongly alkylating agents and the insolubility of the imidazolium salts in this medium. To prevent alkyltriflate hydrolysis the reaction must be conducted under dry argon. Nearly quantitative yields can be obtained.

The syntheses of [$BF_4$] and [$PF_6$] salts were usually prepared using the first route which involves metathesis reaction from the corresponding chloride or bromide salts with $NaBF_4$ and $NaPF_6$ in water (J. D. Holbrey, K. R. Seddon, J. Chem. Soc., dalton Trans. 1999, 2133–2139), methanol (J. S. Wilkes, M. J. Zaworrotko, J. Chem. Soc., Chem. Commun. 1992, 965–967), or acetone.(P. A. Suarez, J. E. L. Dullius, S. Einloft, R. F. de Souza, J. Dupont, Polyhedron, 1996, 15, 1217–1219) They can also be obtained by using other alkylating agents. Those are triethyloxonium tetrafluoroborate and triethyloxonium hexafluorophosphate. As with ethyltriflate, the oxonium salt [$Et_3O$][$BF_4$] reacts with one equivalent of 1,2-dialkyimidazole in refluxing of methylene dichloride with very high yields (H. Olivier, F. Favre. IFP, FR 2.779.143, 1998).

All the imidazolium ionic liquids prepared were air stable under ambient conditions and may be handled under normal laboratory conditions.

Suitable imidazolium salts include for example salts of the following cations: 1,2,3,4,5-pentamethylimidazolium, 1,2,3,5-tetramethyl-4H-imidazolium, 1,2,3,4-tetramethyl-5H-imidazolium, 1-trimethylsilyl-2,3,5-trimethyl-4H-imidazolium, 2,4,5-trichloro- 1,3-dimethylimidazolium, 2,4,5-tribromo-1,3-dimethylimidazolium, 1,2,3-trimethylimidazolium, 1,2-dimethyl-3-ethylimidazolium and 1,2-dimethyl-3-n-butylimidazolium.

Preferred imidazolium salts have 1,2,3-trialkylimidazolium cations.

Among these cations the most preferred cation is 1-n-butyl-2,3-dimethylimidazolium, and the most preferred salts are 1-n-butyl-2,3-dimethylimidazolium bistrifluoromethylsulfonylamide ($BMMI^+TF_2N^-$; liquid at room temperature), and 1-n-butyl-2,3-dimethylimidazolium tetrafluoroborate ($BMMI^+BF_4^-$; liquid at room temperature).

Suitable anions $X^-$ include for example fluoride, chloride, or bromide, hexafluorophosphate, hexafluoroantimonate, hexafluoroarsenate, fluorosulphonate, tetrafluoroborate, bis-perfluoroalkylsulfonyl amides (in particular methyl, butyl and nonyl), and perfluoroalkyl sulfonates (in particular methyl). Tetrachloroborate, tetrachloroaluminate, heptachlorodialuminate ($Al_2Cl_7^-$), and trichliorozincate anions can also be used. The preferred anions are tetrafluoroborate, hexafluorophosphate and bis-trifluoromethylsulfonyl amide.

As mentioned above it is also possible that the phosphorus-containing compound forms the anion of the ionic liquid. Suitable anions are as already mentioned sulfonated or carboxylated alkyl or aryl phosphines or phosphates, the sulfonated phosphines being preferred.

The present invention is further related to the use of a composition comprising at least one transition metal compound, at least one phosphorus-containing compound, and at least one salt selected from the group consisting of 1,2,3-, 1,2,3,4- or 1,2,3,4,5-substituted imidazolium salts and 1-substituted pyridinium salts in a process of telomerizing a conjugated diene. With respect to the preferred embodiments of the components of this composition it is referred to the above description. Preferably the composition is as follows:

The concentration of the transition metal is usually in the range of 1 to 200 mM per liter of ionic liquid and more preferably 10 to 50. The amount of the phosphorous-containing compound is usually 1 to 100, preferably from 1 to 10 mole per mole of the transition metal. The amount of the salt in the reaction system is usually 5 to 100 parts per 100 parts of the diolefine, preferably 10 to 50. The molar ratio of telogen/conjugated diolefin is usually in the range 0.5 to 10, preferably 0.5 to 5.

Regarding the most preferred embodiments of the invention particularly preferred results in the biphasic $C_4H_6$/MeOH or $C_4H_6$/glycol telomerization have been obtained using:

- a palladium transition metal compound, preferably $Pd(OAc)_2$ as the transition metal compound,
- a sulfonated aryl phosphine, preferably TPPMS as the phosphorus-containing compound,
- a 1-butyl-2,3-dimethylimidazolium [BMMI] salt, preferably [BMMI][$TF_2N$] as the salt which forms a liquid under the conditions of the telomerization process, and
- a non-polar solvent, preferably an n-alkane, more preferably n-heptane as cosolvent, preferably under the conditions of:

- a telomerization temperature of 70 to 100° C., preferably 80 to 90° C., more preferably at about 85° C.,
- a molar ratio of the transition metal (preferably Pd) to the phosphorus-containing compound of 1/1 to 1/5, preferably 1/2 to 1/4, more preferably about 1/3 in case of a monodentate phosphorus-containing compound, preferably a sulfonated aryl phosphine,
- a molar ratio of the of the transition metal (preferably Pd) to butadiene, 1/500 to 1/5000, preferably 1/1000 to 1/4000, more preferably about 1/2800, and
- a molar ratio of butadiene to MeOH or glycol of about 2/1.

Particularly preferred results in the biphasic $C_4H_6/H_2O$ telomerization have been obtained using:

- a palladium transition metal compound, preferably $Pd(OAc)_2$ as the transition metal compound,
- a sulfonated aryl phosphine, preferably TPPMS as the phosphorus-containing compound,
- a 1-butyl-2,3-dimethylimidazolium [BMMI] salt, preferably [BMMI][$BF_4$] as the salt which forms a liquid under the conditions of the telomerization process, and
- a non-polar solvent, preferably an n-alkane, more preferably n-heptane as cosolvent, preferably under the conditions of:

- a telomerization temperature of 70 to 100° C., preferably 80 to 90° C., more preferably at about 85° C.,
- in the presence of a tertiary amine, preferably triethyl amine in a ratio of the amine to the transition metal in the transition metal compound, preferably palladium of 10/1 to 100/1, preferably 40/1 to 60/1, more preferably about 50/1,
- a $CO_2$-pressure $P(CO_2)$ of 1 to 10, preferably 3 to 7, more preferably about 5 bar,
- a molar ratio of the transition metal (preferably Pd) to the phosphorus-containing compound of 1/1 to 1/7, preferably 1/2 to 1/6, more preferably about 1/4 in case of a monodentate phosphorus-containing compound, preferably a sulfonated aryl phosphine,
- a molar ratio of the of the transition metal (preferably Pd) to butadiene, 1/500 to 1/4000, preferably 1/1000 to 1/3000, more preferably about 1/1200, and
- a molar ratio of butadiene to $H_2O$ of about 1/1.

These preferred results were achieved for two phase catalytic systems. It is clear to the skilled person in the art that they may be increased under different conditions (e.g. with reaction temperature and/or phosphine ratio modified).

EXAMPLES

A) Preparation of Non-aqueous Ionic Liquids a—Materials

All the syntheses were carried out under dry argon using standard Schlenk techniques. Methylene dichloride was distilled over $P_2O_5$ and stored over 3 Å molecular sieves. All other reagents (1,2-dimethylimidazole, pyridine, $HPF_6$, 1-chlorobutane) were purchased from Aldrich and used as is, unless otherwise indicated.

b—Physicochemical Measurements

Proton and carbon NMR were recorded an a Bruker AC 300 MHz using $CD_2Cl_2$ (from SDS) as solvent and $SiMe_4$ (from Aldrich) as internal standard. Melting point of solid salts was measured an a digital apparatus from Electrothermal.

b—Syntheses

The following salts were prepared according to known procedures (see e.g.: for [EMI][Br], [EMI][$TF_2N$], [EMI][$CF_3SO_3$], [BMI][$TF_2N$]<<Bonhôte, P.; Dias, A.-P.; Papageorgiou, N.; Kalyanasundaram, K.; Gratzel, M. *Inorg. Chem.* 1996, 35, 1168–1178 >>; for [BMI][$BF_4$]<<Holbrey, J. D.; Seddon, K. R. *J. Chem. Soc., Dalton Trans.* 1999, 2133–2139 >>; for [BMI][$PF_6$]<<Suarez, P. A. Z.; Dullius, J. E. L.; Einloft, S.; de Souza, R. F.; Dupont, J. *Polyhedron* 1996,15, 1217–1219.)

$EMI^+Br^-$(1-ethyl-3-methylimidazolium bromide), $EMI^+TF_2N^-$(1-ethyl-3-methylimidazolium bistrifluoromethylsulfonylamide), $EMI^+CF_3SO_3^-$(1-ethyl-3-methylimidazolium trifluoromethylsulfonate), $BMI^+Cl^-$(1-n-butyl-3-methylimidazolium chloride), $BMI^+PF_6^-$(1-n-butyl-3-methylimidazolium hexafluorophosphate), $BMI^+TF_2N^-$(1-n-butyl-3-methylimidazolium bistrifluoromethylsulfonylamide), and $BMI^+BF_4^-$(1-n-butyl-3-methylimidazolium tetrafluoroborate).

Preparation Example 1

1-butyl-2,3-dimethylimidazolium chloride [BMMI][Cl]: Freshly distilled 1-chlorobutane (88 g, 0.96 mol) was added in one portion to a 500 ml thick walled glass reactor equipped with a magnetic stirrer containing 1,2-dimethylimidazole (65 g, 0.68 mol). The reactor was sealed and the solution was stirred for 16 h at 100° C. (note: the reaction pressure was in excess of 2 atm). Reactor was degassed and the hot solution was transferred (under argon) in a round bottom flask containing acetonitrile (95 ml). The solution was added dropwise under vigorous stirring to toluene (500 ml). A precipitate formed and was filtered, washed with toluene (3×100 ml) and dried overnight under vacuum. [BMMI][Cl] was obtained (89.73 g, 70% yield) as a white hygroscopic solid. $^1H$ NMR ($CD_2Cl_2$): δ0.97 [t, $^3J$=7.15 Hz, $NCH_2CH_2CH_2CH_3$]; 1.39 [sext, $^3J$=7.5 Hz, $NCH_2CH_2CH_2CH_3$]; 1.80 [quint, $^3J$=7.4 Hz, $NCH_2CH_2CH_2CH_3$]; 2.75 [s, $CCH_3$]; 4.00 [s, $NCH_3$]; 4.19 [t, $^3J$=7.1 Hz, $NCH_2CH_2CH_2CH_3$]; 7.52 [s, $CH$]; 7.84 [s, $CH$]; $^{13}C$ NMR ($CD_2Cl_2$): δ10.70 [$NCH_2CH_2CH_2CH_3$]; 13.74 [$NCH_2CH_2CH_2CH_3$]; 19.96 [$NCH_2CH_2CH_2CH_3$]; 32.26 [$CCH_3$]; 36.09 [$NCH_3$]; 48.94 [$NCH_2CH_2CH_2CH_3$]; 121.72 [$CH$]; 123.64 [$CH$]; 144.03 [$CCH_3$]; Elemental analysis (calculated): %C=57.14 (57.29); %H,=9.08 (9.08); %N=14.85 (14.85); Mp=104–105° C.

Preparation Example 2

1-butyl-2,3-dimethylimidazolium bistrifluoromethylsulfonylamide [BMMI][$TF_2N$]: A solution of lithium bis((trifluoromethyl)sulfonyl)amide (41.9 g, 0.149 mol) in 100 ml of $H_2O$ was added dropwise to a solution of [BMMI][Cl] (24.32 g, 0.129 mol) in 150 ml of $H_2O$. The solution was stirred at 70° C. for 2 h and then cooled to room temperature. Methylene dichloride (50 ml) was added, and all was transferred to a separatory funnel. The lower phase (ionic liquid+$CH_2Cl_2$) was collected. Ionic liquid was purified through a short alumina column, and the $CH_2Cl_2$ removed on a Rotavapor. The resultant hydrophobic liquid was washed 3 times with 150 ml of $H_2O$ and dried for 3 h at 50° C. under vacuum to afford [BMMI][$TF_2N$] (44.1 g, 78.9% yield) as a colorless liquid. $^1H$ NMR ($CD_2Cl_2$): δ0.97 [t, $^3J$=7.15 Hz, $NCH_2CH_2CH_2CH_3$]; 1.37 [sext, $^3J$=7.5 Hz, $NCH_2CH_2CH_2CH_3$]; 1.78 [quint, $^3J$=7.4 Hz, $NCH_2CH_2CH_2CH_3$]; 2.59 [s, $CCH_3$]; 3.79[s, $NCH_3$]; 4.04 [t, $^3J$=7.1 Hz, $NCH_2CH_2CH_2CH_3$]; 7.19 [s, $CH$]; 7.21 [s, $CH$]; $^{13}C$ NMR ($CD_2Cl_2$): δ9.78 [$NCH_2CH_2CH_2CH_3$]; 13.53 [$NCH_2CH_2CH_2CH_3$]; 19.86 [$NCH_2CH_2CH_2CH_3$]; 31.90 [$CCH_3$]; 35.60 [$NCH_3$]; 49.00 [$NCH_2CH_2CH_2CH_3$]; 121.37 [$CH$]; 122.91 [$CH$]; 144.21 [$CCH_3$]; 120.50 [q, $J_{C-F}$=321.4 Hz, ($CF_3SO_2$)$_2N$]; Elemental analysis (calculated): %C=30.68 (30.49); %H=3.96 (3.95); %N=9.66 (9.70); %Cl<250 ppm (0).

Preparation Example 3

1-butyl-2,3-dimethylimidazolium tetrafluoroborate [BMMI][$BF_4$]: Procedure previously described for the synthesis of [BMMI][$TF_2N$] was used (except the washes with water). From 22.23 g (0.118 mol) of [BMMI][Cl] and 15.52 g (0.141 mol) of sodium tetrafluoroborate, there were obtained 25.33 g (90% yield) of [BMMI][$BF_4$] as a colorless, very viscous and hydrophilic liquid. $^1H$ NMR ($CD_2Cl_2$): δ0.96 [t, $^3J$=7.15 Hz, $NCH_2CH_2CH_2CH_3$]; 1.38 [sext, $^3J$=7.5 Hz, $NCH_2CH_2CH_2CH_3$]; 1.78 [quint, $^3J$=7.4 Hz, $NCH_2CH_2CH_2CH_3$]; 2.60 [s, $CCH_3$]; 3.80 [s, $NCH_3$]; 4.06 [t, $^3J$=7.1 Hz, $NCH_2CH_2CH_2CH_3$]; 7.25 [dd, $CH$]; 7.30 [dd, $CH$]; $^{13}C$ NMR ($CD_2Cl_2$): δ9.58 [$NCH_2CH_2CH_2CH_3$]; 13.61 [$NCH_2CH_2CH_2CH_3$]; 19.79 [$NCH_2CH_2CH_2CH_3$]; 31.94 [$CCH_3$]; 35.36 [$NCH_3$]; 48.70 [$NCH_2CH_2CH_2CH_3$]; 121.30 [$CH$]; 122.88 [$CH$]; 144.31 [$CCH_3$]; Elemental analysis (calculated): %C=45.09 (45.03); %H=7.25 (7.14); %N=11.52 (11.67); %Cl=0.11 (0).

Preparation Example 4

1-butylpyridinium chloride [BuPy][Cl]: Procedure previously described for the synthesis of [BMMI][Cl] was used. From 48.9 g (0.618 mol) of pyridine and 57.4 g (0.62 mol) of 1-chlorobutane, [BuPy] [Cl](85.4 g, 80.5% yield) was obtained as a white solid. $^1H$ NMR ($CD_2Cl_2$): δ0.97 [t, $^3J$=7.4 Hz, $NCH_2CH_2CH_2CH_3$]; 1.42 [sext, $^3J$=7.7 Hz, $NCH_2CH_2CH_2CH_3$]; 2.04 [quint, $^3J$=7.6 Hz, $NCH_2CH_2CH_2CH_3$]; 5.06 [t, $^3J$=7.4 Hz, $NCH_2CH_2CH_2CH_3$]; 8.14 [t, $^3J$=7.2 Hz, 2 $CH_{ar}$]; 8.51 [t, $^3J$=7.7 Hz, 1$CH_{ar}$]; 9.76 [d, $^3J$=5.5 Hz, 2$NCH_{ar}$]; $^{13}C$ NMR ($CD_2Cl_2$): δ13.62 [$NCH_2CH_2CH_2CH_3$]; 19.46 [$NCH_2CH_2CH_2CH_3$]; 34.13 [$NCH_2CH_2CH_2CH_3$]; 61.21 [$NCH_2CH_2CH_2CH_3$]; 128.53 [$2CH_{ar}$]; 145.48 [$1CH_{ar}$]; 145.87 [$2NCH_{ar}$]; Elemental analysis (calculated): %C=59.47 (62.97); %H=8.62 (8.22); %N=7.91 (8.16). Mp=137–138° C.

Preparation Example 5

1-butylpyridinium hexafluorophosphate [BuPy][$PF_6$]: A solution of hexafluorophosphoric acid (60% wt in water) (10 cm$^3$) was added dropwise to a solution of [BuPy][Cl] (5.77 g, 33.6 mmol) in 100 ml of distilled water. The solution was stirred at room temperature for 1 h. The white precipitate formed was filtered off, washed several times with 50 ml of $H_2O$ and dried overnight at room temperature under vacuum to afford [BuPy][$PF_6$] (4.45 g, 47.1% yield) as a white solid. $^1H$ NMR ($CD_2Cl_2$): δ0.99 [t, $^3J$=7.4 Hz, $NCH_2CH_2CH_2C$ H₃]; 1.41 [sex, $^3J$=7.5 Hz, NCH₂CH₂CH₂CH₃]; 2.01 [quint, $^3J$=7.6 Hz, NCH₂CH₂CH₂CH₃]; 4.58 [t,$^3J$=7.4 Hz, NCH₂CH₂CH₂CH₃]; 8.08 [t, $^3J$=6.9 Hz, 2 CH$_{ar}$]; 8.51 [t, $^3J$=7.7 Hz, 1CH$_{ar}$]; 8.68 [d, $^3J$=5.5 Hz, 2NCH$_{ar}$]; $^{13}C$ NMR (CD₂Cl₂): δ13.38 [NCH₂CH₂CH₂CH₃]; 19.58 [NCH₂CH₂CH₂CH₃]; 33.56 [NCH₂CH₂CH₂CH₃]; 62.81 [NCH₂CH₂CH₂CH₃]; 129.06 [2 CH$_{ar}$]; 144.34 [1 CH$_{ar}$]; 146.05 [2 NCH$_{ar}$]; Elemental analysis (calculated): %C=38.70 (38.44); %H=5.09 (5.02); %N=5.06 (4.98). Mp=78–79° C.

B) Catalysis a—Materials

Pd(OAc)₂ (98%) was purchased from Strem Chemicals, stored under argon and used without further purification. Triphenylphosphine (PPh₃) was obtained from Aldrich, trisodium tris(m-sulfonatophenyl)phosphine) (TPPTS) from the lab reserves (this salt can be prepared according to U.S. Pat. No. 4,142,060), bis(p-sulfonatophenyl)phenylphosphine dihydrate dipotassium salt (TPPDS) from Strem Chemical and diphenylphosphinobenzene-3-sulfonic acid sodium salt (TPPMS) from TCI. Those phosphines were stored under argon and used as is. Butadiene (N25) and CO₂ (N25) were obtained from Air-liquide >> and used directly from cylinders. Methanol used in all experiments is obtained by refluxing over Mg/I₂, and stored over 3 Å molecular sieves. Heptane was distilled over Na/K and stored over 3 Å molecular sieves under argon.

b—Catalytic Experiments and Analyses

Catalytic runs: All catalytic reactions were performed in a 100 ml magnetically stirred stainless steel autoclave equipped with an inner glass beaker and an internal thermocouple under argon atmosphere as shown in FIG. 1. In a typical reaction, Pd(OAc)₂, phosphine, ionic liquid, alcohol and eventually heptane are introduced in a Schlenk and then transferred into the purged autoclave via a ball valve. The autoclave is cooled to T<<–10° C. and the desired mass of butadiene is transferred from a lecture bottle resting an a scale. In case of the telomerisation with water (catalysis examples 17 and 18) a pressure of 5 bar CO₂ was introduced. The reactor is then heated to the desired reaction temperature. After the selected reaction time, the autoclave is cooled to 40° C. and butadiene is condensed in a volumetric cylinder cooled to –78° C. The volume of the liquid condensed in the cylinder (determined to be almost pure butadiene) is noted. The autoclave is then warmed to room temperature. The remaining liquid phases in the autoclave are recovered, weighed and further analyzed (GC, GC-MS, NMR, etc.). Thus there were two measures of butadiene conversion, from the volume of unreacted butadiene (condensed in the graduated cylinder) and the change in the weight increase of the liquid solutions in the autoclave.

Work-up: When at the end of the run only a single liquid phase was present, a sample was analyzed without further treatment. When multiple phases were present, only the upper phase was analyzed for product.

Analyses: The identification of the telomerization products was carried out both by HewlettPackard GCD and NMR analyses. Finally they were quantitatively analyzed by gas chromatography an a HP6890 chromatograph equipped with FID detector and a HP1 column (L=30 m, $\phi_{int}$=0.32 mm, film thickness=0.25 μm.) Injection temperature was 170° C. and detector temperature was 180° C. The temperature program was from 60° C. (3 mn (minutes)) to 100° C. (0 mn) at a heating rate of 10° C./mn to 220° C. (30 mn) at a heating rate of 5° C./mn.

c—Data Presentation

Abbreviations

OT: 1,3,7-octatriene and 1,3,6-octatriene

VCH: 4-vinyl-cyclohexene

Oligo.: products containing three and more units of butadiene

1-OMe: (cis+trans)-1-methoxy-2,7-octadiene

3-OMe: 3-methoxy-1,7-octadiene

1-Ol: 1-hydroxy-2,7-octadiene

3-Ol: 3-hydroxy-1,7-octadiene

1-OGly: (cis+trans) 1-hydroxy-2-(2,7-octadienyl-1-oxy)ethane

3-OGly: 1-hydroxy-2-(1,7-octadienyl-3-oxy)ethane

Conversions and Selectivities are Defined by the Following Equations (In case that other dienes than butadiene are reacted butadiene needs to be replaced by the corresponding conjugated diene.)

Conv. A % is calculated from unreacted butadiene remaining after reaction $$\text{Conv. A} = \frac{\text{mass of butadiene introduced} - \text{mass of butadiene recovered}}{\text{mass of butadiene introduced}}$$

Conv. B % is calculated from the increase in the mass of the reactor $$\text{Conv. B} = \frac{\text{increase of the mass of reactor contents}}{\text{mass of butadiene introduced}}$$

Selectivities toward products are evaluated as:

$$\text{GC. Sel.} = \frac{\text{moles of product}}{\sum(\text{moles of product})}$$

Furthermore, selectivities to linear telomers (in the tables comprehensively reported as Ratio 1/3) are evaluated as $$\text{Ratio 1/3} = \frac{\text{moles of linear C8 compounds}}{\text{moles of branched C8 compounds}}$$

For example in the following reaction scheme Ratio 1/3 would correspond to the ratio (A)/(B):

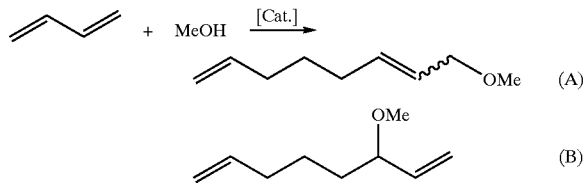

Turn over number in mol C₄H₆/mol Pd is evaluated as $$\text{TON} = \frac{\text{mole of butadiene converted}}{\text{moles of palladium}} \text{(average of Conv. A and Conv. B)}$$

Material Balance $$MB = \frac{(\text{mass of initial butadiene} - \text{mass increase}) + \text{mass of butadiene in products}}{\text{mass of initial butadiene}}$$

Material balance varied in the range of 80–100%. No perfect mass balance was obtained especially when two-phase liquid-liquid systems are obtained, certainly due to the partitioning of reaction products between the two phases of the system (only the organic phase was analyzed).

Determination of the Palladium Leaching in the Organic Phase $$\% \text{ Pd leaching} = \frac{\text{mass of Pd in the organic phase}}{\text{mass of initial palladium}}$$

The analytical procedure consists in evaporate the organic products and solubilize the residue in a melt of $HNO_3/HCl$. Palladium contained in this mixture is then quantified by ICP/SM.

d—Catalysis Examples (Cat. Ex.) and Comparative Catalysis Examples (Comp. Cat. Ex.)

Using the telomerization apparatus described above catalysis examples and comparative catalysis were carried out under the conditions indicated in the following.

Catalysis Examples 1 to 3

Catalysis examples 1 to 3 for telomerizing 1,3-butadiene with methanol were run using $Pd(OAc)_2/PPh_3$ as the catalyst system. Table 1 shows the results.

TABLE 1

Telomerization of 1,3-butadiene with methanol in the presence of $Pd(OAc)_2PPh_3$[a]

| Cat. Ex. | Ionic Liquid | Conv A | Conv B | Time (h) | 1-OMe + 3-OMe | GC Sel. (mol %) VCH | OT | Olig. | Ratio 1/3 | MB (% mol) | TON |
|---|---|---|---|---|---|---|---|---|---|---|---|
| 1 | BuPy$^+$PF6$^{-[b]}$ | 100 | 81 | 5 | 56.8 | 1.0 | 28.1 | 14.1 | 18.2 | 71 | 2403 |
| 2 | BMMI$^+$BF4$^-$ | 100 | 92 | 1 | 81.8 | 0.2 | 15.1 | 2.9 | 8.1 | 85 | 2619 |
| 3 | BMMI$^+$TF$_2$N$^-$ | 100 | 89 | 1 | 84.0 | 0.2 | 13.7 | 2.1 | 8.5 | 81 | 2537 |

[a]Reaction conditions: $Pd(OAc)_2$, = 30 mg (0.134 mmol); $PPh_3$ = 105 mg (0.400 mmol); Ionic liquid (4 ml); MeOH = 15 ml (370 mmol); $C_4H_6$ = 20 g (mol); T = 85° C.;
[b]1.63 g (5.80 mmol) of BuPy$^+$PF6$^-$ (white solid).

For the pyridinium salt (Cat. Ex. 1), the reaction was complete after 5 h. The selectivity toward telomers was relatively low (56.8%) and formation of palladium black was observed. On the other hand the regioselectivity indicated by the 1-OMe/3-OMe ratio was high (18.2%).

The best results were found for the 1,2,3-trialkylimidazolium ionic liquids regarding conversions and reaction rates (Cat. Ex. 2 and 3). Quantitative conversions were achieved after 1 h for the two solvents studied. Selectivities toward telomers are around 83% and, again, there is a favorable effect an the regioselectivity of the telomerisation reaction, the ratio 1-OMe/3-OMe in excess of 8. It seems that the nature of the anion of the salts (between the hydrophobic $TF_2N^-$ salt and the hydrophilic $BF4^-$ salt) does not induce any notable difference in terms of activity and selectivity.

Furthermore, at the end of these reaction, absolutely no palladium black was observed. A two-phase liquid-liquid system remains. The lower phase corresponds to the ionic liquid whereas the upper one is a mixture of products and unreacted methanol.

Catalysis Examples 4 to 6

Catalysis example 4 to 6 were run using $Pd(OAc)_2$ and water-soluble TPPMS as catalyst system. The results are shown in table 2.

TABLE 2

Telomerization of 1,3-butadiene with methanol in the presence of Pd(OAc)$_2$/TPPMS[a]

| Cat. Ex. | Pd(OAc)$_2$ (mmol) | Temp. °C. | Time (h) | Conv A | Conv B | GC Sel. (mol %) 1-OMe + 3-OMe | VCH | OT | Olig. | Ratio 1/3 | MB (% mol) | TON |
|---|---|---|---|---|---|---|---|---|---|---|---|---|
| 4 | 0.134 | 85 | 1 | 100 | 93 | 77.9 | 0.3 | 17.1 | 4.7 | 13.7 | 81 | 2769 |
| 5 | 0.028 | 85 | 5.75 | 85 | 80 | 77.7 | 0.8 | 20.9 | 0.6 | 16.0 | — | 11092 |
| 6 | 0.025 | 110 | 5.75 | 89 | 75 | 50.4 | 3.0 | 41.8 | 4.8 | 11.7 | — | 11953 |

[a]Reaction conditions: TPPMS = 3 eq/Pd; BMMI$^+$TF$_2$N$^-$ (4 ml): MeOH = 15 ml (370 mmol); C$_4$H$_6$ = 20 g (370 mmol);

The use of TPPMS lead to a single phase system at 93% conversion (Cat. Ex. 4). Selectivity toward telomers is lower with TPPMS than with TPP, 77.9 against 84.0. However with TPPMS the ratio 1-OMe/3-OMe is largely better, 13.7. The addition of 16%wt (10 ml) of heptane to the solution obtained in Cat. Ex. 4 lead to clean separation of an ionic liquid phase from the product/MeOH/heptane phase.

Catalysis Example 7 to 9

Catalysis examples 7 to 9 were run in the presence of n-heptane using Pd(OAc)$_2$ and different phosphines. The palladium leaching into the organic phase was determined by microanalysis of the two phases. The results are shown in table 3.

TABLE 3

Telomerization of 1,3-butadiene with methanol in the presence of n-heptane using Pd(OAc)$_2$ and different phosphines[a]

| Cat. Ex. | Phosphine | Conv A | Conv B | Time (h) | GC Sel. (mol %) 1-OMe + 3-OMe | VCH | OT | Olig. | Ratio 1/3 | % Pd leaching | TON |
|---|---|---|---|---|---|---|---|---|---|---|---|
| 7 | TPP | 82 | 71 | 3 h | 53.3 | — | 40.6 | 6.1 | 14.6 | 14.2 | 2127 |
| 8 | TPPMS | 74 | 66 | 3 h | 70.3 | 0.6 | 14.1 | 15.0 | 13.1 | 1.9 | 1816 |
| 9 | TPPDS | 56 | 51 | 3 h | 58.6 | 1.2 | 17.5 | 22.8 | 15.0 | 1.8 | 1373 |

[a]Reaction conditions: Pd(OAc)$_2$ = 30 mg (0.134 mmol): Phosphine = 3 eq/Pd; [BMMI][TF$_2$N] (4 ml); MeOH = 7.5 ml (185 mmol); heptane = 10 ml; C$_4$H$_6$ = 20 g (370 mmol); T = 85° C.;

Catalysis Examples 10 to 14

The product phase of catalysis example 8 was decanted and the palladium contained in the ionic liquid phase was reintroduced to the reactor with fresh reactants and co-solvent. Microanalysis of the organic phase at the end of each catalysis example 10 to 14 indicates generally 1–4% leaching of palladium to the organic phase. Slight changes in activity were observed with each cycle. At first, activities are actually higher (catalysis examples 10 to 12) perhaps as the initiation reactions (conversion of Pd(OAc)$_2$ to the active species) reach completion. Activity slowly degrades in catalysis examples 13 and 14, in part perhaps due to the mechanical difficulty of quantitatively recuperating the ionic liquid phase (drops of the liquid can remain in the schlenk tube used for decantation and/or the syringe), palladium leaching, or to some palladium deactivation. In no case was there obvious evidence for the formation of palladium black. The results are shown in table 4.

TABLE 4

Telomerization of 1,3-butadiene with methanol in the presence of n-heptane using recycled ionic liquid phase[a]

| Cat. Ex. | Conv A | Conv B | GC Sel. (mol %) 1-OMe + 3-OMe | VCH | OT | Olig. | Ratio 1/3 | MB (% mol) | TON |
|---|---|---|---|---|---|---|---|---|---|
| 10 | 74 | 66 | 70.3 | 0.6 | 14.1 | 15.0 | 13.1 | 79 | 1816 |
| 11 | 82 | 73 | 72.2 | 0.5 | 13.2 | 14.2 | 12.4 | 81 | 2001 |

TABLE 4-continued

Telomerization of 1,3-butadiene with methanol in the presence of n-heptane using recycled ionic liquid phase[a]

| Cat. Ex. | Conv A | Conv B | GC Sel. (mol %) | | | | Ratio 1/3 | MB (% mol) | TON |
|---|---|---|---|---|---|---|---|---|---|
| | | | 1-OMe + 3-OMe | VCH | OT | Olig. | | | |
| 12 | 89 | 81 | 72.4 | 0.4 | 15.9 | 11.3 | 15.4 | 77 | 2249 |
| 13 | 80 | 68 | 75.6 | 0.5 | 16.2 | 7.7 | 16.3 | 83 | 1907 |
| 14 | 70 | 63 | 78.8 | 0.9 | 17.3 | 3.1 | 18.6 | 82 | 1709 |

[a]Reaction conditions: $Pd(OAc)_2$, = 30 mg (0.134 mmol); TPPMS = 3 eq/Pd; $BMMI^+$ $(CF_3SO_2)_2N^-$ (4 ml); MeOH = 7.5 ml (185 mmol); heptane = 10 ml; $C_4H_6$ = 20 g (370 mmol); T = 85° C.; t = 3 h.

Comparative Catalysis Examples 1 to 4

Comparative catalysis examples 1 to 4 were run using 1,3-dialkylimidazolium salts. The results are shown in table 5.

Comparative Catalysis Examples 5 to 8

Comparative Catalysis examples 5 to 8 were run using 1,3-dialkylimidazolium salts and different phosphine/palladium ratios in order to determine their influence on the conversion and selectivity. The results are shown in table 6.

TABLE 5

Telomerization of 1,3-butadiene with methanol using $Pd(OAc)_2/PPh_3$ as a catalyst system in the presence of 1,3-dialkylimidazolium salts as ionic liquid[a]

| Comp. Cat. Ex. | Ionic Liquid | Conv A | Conv B | GC Sel. (mol %) | | | | ratio 1/3 | MB | TON |
|---|---|---|---|---|---|---|---|---|---|---|
| | | | | 1-OMe + 3-OMe | VCH | OT | Olig. | | | |
| 1 | $BMI^+TF_2N^-$ | 10 | 7 | 62.0 | 18.4 | 3.5 | 16.1 | 7.8 | 95 | 241 |
| 2 | $BMI^+BF_4^-$ | 15 | -1 | 49.6 | 1.2 | 33.9 | 15.4 | 5.8 | 104 | 165 |
| 3 | $EMI^+TF_2N^-$ | 7 | 0 | 27.5 | 44.7 | 0.6 | 27.1 | 6.5 | 97 | 271 |
| 4 | $EMI^+TF_2N^-$ | 7 | 0 | 28.6 | 63.0 | 1.5 | 6.8 | 5.1 | 104 | 106 |

[a]Reaction conditions: $Pd(OAc)_2$ = 30 mg (0.134 mmol); $PPh_3$ = 105 mg (0.400 mmol); Ionic liquid (1 ml); MeOH = 15 ml (370 mmol); $C_4H_6$ = 20 g (370 mmol); T = 85° C.; t = 22 h.

TABLE 6

Telomerization of 1,3-butadiene with methanol using $Pd(OAc)_2/PPh_3$ with different Pd/phosphine ratios as a catalyst system in the presence of 1,3-dialkylimidazolium salts as ionic liquid[a]

| Comp. Cat. Ex. | Phosphine/ Pd-ratio | Conv A | Conv B | GC Sel. (mol %) | | | | Ratio 1/3 | MB (% mol) | TON |
|---|---|---|---|---|---|---|---|---|---|---|
| | | | | 1-OMe + 3-OMe | VCH | OT | Olig. | | | |
| 5 | 3 | 11 | 1 | 56.2 | 32.9 | 1.7 | 9.2 | 5.9 | 104 | 166 |
| 6 | 4 | 11 | 5 | 72.9 | 27.1 | — | — | 5.9 | 101 | 228 |
| 7 | 10 | 26 | 19 | 73.0 | 9.9 | — | 17.1 | 6.5 | 98 | 593 |
| 8 | 20 | 30 | 23 | 71.0 | 12.7 | 2.3 | 14.0 | 6.5 | 96 | 745 |

[a]Reaction conditions: $Pd(OAc)_2$ = 30 mg (0.134 mmol); $EMI^+TF_2N^-$ (1 ml); MeOH = 15 ml (370 mmol); $C_4H_6$ = 20 g (370 mmol); T = 85° C.; t = 22 h Conversions were extremely low, if indeed there was any conversion at all. The absence of reaction is not concomitant with the formation of palladium black. Systems at the end of the reaction appears as homogeneous quite colorless liquids. The possible contamination of halide impurities from the ionic liquid can be totally excluded since the halide contents of ionic liquids were always under the detection limit (50 ppm) which constitutes would be too little for total contamination of the catalyst.

Even with a large excess of $PPh_3$ performances of the catalytic system remains very low. With 20 equivalents of phosphine per palladium, conversion does not exceed 26% (Comp. Cat. Ex. 8).

Catalysis Examples 15 and 16

Catalysis examples 15 to 16 for telomerizing 1,3-butadiene with glycol in the presence of n-heptane were run using $Pd(OAc)_2/TPPMS$ as the catalyst system. Table 7 shows the results.

TABLE 7

Telomerization of 1,3-butadiene with glycol in the presence of n-heptane using Pd(OAc)$_2$/TPPMS as a catalyst system[a]

| Cat. Ex. | Conv A | Conv B | 1-Ogly + 3-OGly | VCH | OT | Olig. | Ratio 1/3 | TON |
|---|---|---|---|---|---|---|---|---|
| 15[b] | 96 | 87 | 67.6 | 5.2 | 4.2 | 1.7 | 24.0 | 2767 |
| 16[c] | 93 | 81 | 79.9 | — | 6.9 | — | 26.4 | 2482 |

[a]Reaction conditions: Pd(OAc)$_2$ = 30 mg (0.134 mmol); Phosphine = 3 eq/Pd, BMMI$^+$TF$_2$N$^-$ (1 ml); glycol = 10.5 g (190 mmol); C$_4$H$_6$ = 20 g (370 mmol); T = 85° C.; t = 0.75 h
[b]heptane 10 ml
[c]heptane 30 ml

Catalysis Examples 17 and 18

Catalysis examples 17 and 18 for telomerizing 1,3-butadiene with water was run using Pd(OAc)$_2$/TPPMS as the catalyst system. Table 8 shows the results.

TABLE 8

Telomerization of 1,3-butadiene with water using Pd(OAc)$_2$/TPPMS as a catalyst system[a]

| Cat. Ex. | Amine | Heptane (ml) | Time (h) | Conv A | Conv B | 1- + 3- Octa-dienols | VCH | OT | Olig. | Ratio 1/3 | TON |
|---|---|---|---|---|---|---|---|---|---|---|---|
| 17 | NEt$_3$ | — | 3 | 95 | 95 | 74.0 | 0 | 18.8 | 7.2 | 18.0 | 1164 |
| 18 | NEt$_3$ | 30 | 5 | 78 | 70 | 67.9 | <0.1 | 32.1 | <0.1 | 18 | 961 |

[a]Reaction conditions: Pd(OAc)$_2$ = 50 mg (0.223 mmol); TPPMS = 4 eq/Pd (324 mg (0.892 mmol)), BMMI$^+$BF$_4^-$ (4 ml); H$_2$O = 5 g (278 mmol); C$_4$H$_6$ = 15 g (278 mmol); T = 85° C.; CO$_2$ = 5 bar; NEt$_3$ = 50 eq/Pd.

In accordance with present invention a new process for telomerizing conjugated dienes is provided which allows to use a highly active and selective catalyst which can be separate and recycled by a simple procedure.

What is claimed is:

1. A process for telomerizing a conjugated diene comprising the step of:
    reacting said conjugated diene with a compound containing active hydrogen in the presence of a catalyst system comprising at least one transition metal compound, at least one phosphorus-containing compound, and at least one salt which forms a liquid under the conditions of the telomerization process, and
    the phosphorus-containing compound is selected from the group consisting of mono- or bidentate alkylphosphines, arylphosphines, arylalkylphosphines, alkylphosphites, arylphosphites, and arylalkylphosphites, wherein the hydrocarbon moieties independently each may have up to 36 carbon atoms and may be substituted by one to three suitable substituents.

2. The process according to claim 1, wherein the compound containing active hydrogen is a compound of the general formula (I)

$$H-A \quad (I)$$

wherein A is selected from the group consisting of hydroxy, alkoxy, cycloalkoxy, alkoxy substituted with one or two hydroxy groups, hydroxypolyalkyleneoxy, alkenyloxy, aryloxy, alkanoyloxy, mono- or dialkylamino, tri(alkyl and/or aryl)silyl and an alkyl group substituted in the α-position with at least one electron attracting group, wherein the above mentioned alkyl moieties independently from each other are branched or linear and each may have up to 8 carbon atoms, and wherein the above mentioned aryl moieties independently from each other may have up to 10 carbon atoms.

3. The process according to claim 1 wherein the transition metal compound is selected from at least one element of the group VIIIB of the periodic system of elements.

4. The process according to claim 3, wherein the transition metal compound is a palladium compound.

5. The process according to claim 1, wherein the phosphorus-containing compound is selected from sulfonated arylphosphines and salts thereof.

6. The process according to claim 1, which comprises adding at least one non-polar solvent at any stage of the process.

7. The process according to claim 1, which comprises reacting said conjugated diene with a compound containing active hydrogen in the presence of a catalyst system comprising at least one transition metal compound, at least one phosphorus-containing compound, and at least one salt which forms a liquid under the conditions of the telomerization process, optionally adding at least one non-polar solvent during or after the reaction, separating the product phase and the salt phase comprising the catalyst system and recycling the salt phase comprising the catalyst system in the telomerization reaction.

8. The process according to claim 1, wherein the salt has a melting point of below 200° C.

9. The process according to claim 1, wherein the salt is selected from the group consisting of 1,2,3-, 1,2,3,4- or 1,2,3,4,5-substituted imidazolium salts and 1-substituted pyridinium salts.

10. A process of telomerizing a conjugated diene, comprising the steps of:
    providing a transition metal compound, a phosphorus-containing compound, and a salt selected from the group consisting of 1,2,3-, 1,2,3,4- or 1,2,3,4,5-substituted imidazolium salts and 1-substituted pyridinium salts;
    providing a conjugated diene; and
    reacting said conjugated diene with said transition metal compound, said phosphorus-containing compound and said salt so as to form a telomer.